US012612584B2

(12) United States Patent
Kim et al.

(10) Patent No.: US 12,612,584 B2
(45) Date of Patent: Apr. 28, 2026

(54) ELECTROCEUTICAL SCREENING DEVICE AND SCREENING METHOD USING SAME

(71) Applicant: DAEGU GYEONGBUK INSTITUTE OF SCIENCE AND TECHNOLOGY, Daegu (KR)

(72) Inventors: Min Seok Kim, Daegu (KR); Hyun Gyu Kang, Jeju-si (KR); Woon Hae Kim, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 559 days.

(21) Appl. No.: 18/019,854

(22) PCT Filed: Apr. 27, 2021

(86) PCT No.: PCT/KR2021/005278
§ 371 (c)(1),
(2) Date: Feb. 6, 2023

(87) PCT Pub. No.: WO2022/030729
PCT Pub. Date: Feb. 10, 2022

(65) Prior Publication Data
US 2023/0279325 A1 Sep. 7, 2023

(30) Foreign Application Priority Data
Aug. 4, 2020 (KR) ........................ 10-2020-0097284

(51) Int. Cl.
*C12M 1/42* (2006.01)
*C12M 3/06* (2006.01)

(52) U.S. Cl.
CPC .............. *C12M 23/16* (2013.01); *C12M 1/42* (2013.01); *C12M 35/02* (2013.01)

(58) Field of Classification Search
CPC ........ C12M 23/16; C12M 1/42; C12M 35/02; C12N 5/06; C12N 5/0619; C12N 2503/02; G01N 33/50; G01N 33/5005
(Continued)

(56) References Cited

U.S. PATENT DOCUMENTS

2012/0004144 A1* 1/2012 Perroud ............ B01L 3/502761
506/39

FOREIGN PATENT DOCUMENTS

EP 0 689 051 A2 * 12/1995 .......... G01N 33/487
JP 4421445 B2 2/2010
(Continued)

OTHER PUBLICATIONS

International Search Report dated Nov. 5, 2021 for corresponding International Patent Application No. PCT/KR2021/005278, 7 pages.
(Continued)

*Primary Examiner* — Christine T Mui
(74) *Attorney, Agent, or Firm* — Hauptman Ham, LLP

(57) ABSTRACT
The present invention relates to an electroceutical screening device and a screening method using same, respectively, wherein an electrical stimulation is applied, through the electrodes, to the cell clusters received in the channels, and the potentials of the cell clusters are measured so as to measure neural activity, and thus electrical stimulation tests are conducted in various ways, and by measuring conduction velocity according to the various electrical stimulation tests, conditions for electrical stimulation therapy are assessed.

11 Claims, 10 Drawing Sheets

(58) Field of Classification Search
USPC ................................................. 422/502, 500
See application file for complete search history.

(56) References Cited

FOREIGN PATENT DOCUMENTS

| KR | 10-0150390 B1 | 10/1998 |
| KR | 10-2000-0022329 A | 4/2000 |
| KR | 10-2002-0086625 A | 11/2002 |
| KR | 10-0564683 B1 | 3/2006 |

OTHER PUBLICATIONS

Written Opinion dated Nov. 5, 2021 for corresponding International Patent Application No. PCT/KR2021/005278, 4 pages.
Bruno et al., "Microfluidic Multielectrode Arrays for Spatially Localized Drug Delivery and Electrical Recordings of Primary Neuronal Cultures," Frontiers in Bioengineering and Biotechnology, Jun. 16, 2020, vol. 8, Article 626, 11 pages.

* cited by examiner

SUBSTRATE

PDMS MICROFLUIDIC CHIP

SUBSTRATE     PDMS MICROFLUIDIC CHIP

Y
Z → X

THIRD ELECTRODES (E3n ~ E3m)

CHANNEL

SECOND ELECTRODES(E2n ~ E2m)

PDMS MICROFLUIDIC CHIP

FIRST ELECTRODE(E1)(NOT ILLUSTRATED)

BUFFER UNIT

GUIDE BLOCK

ELECTROCEUTICAL SCREENING DEVICE AND SCREENING METHOD USING SAME

CROSS-REFERENCE TO RELATED APPLICATION

The present application is a national stage filing under 35 U.S.C § 371 of PCT application number PCT/KR2021/005278 filed on Apr. 27, 2021 which is based upon and claims the benefit of priorities to Korean Patent Application No. 10-2020-0097284 filed on Aug. 4, 2020 in the Korean Intellectual Property Office. All of the aforementioned applications are hereby incorporated by reference in their entireties.

TECHNICAL FIELD

The present disclosure relates to an electroceutical screening device and a screening method using the same, and to an electroceutical screening device for identifying and selecting an effective electrical stimulation conditions for neuro therapy electroceuticals and a screening method using the same.

BACKGROUND ART

Nerve is a neuropathic organization that connects each organ system and is responsible for adjusting physical activity as one organism, and human nerves are composed of nets of neurons, and external stimuli of a human body is accepted through a sensory nervous system and passed through a spinal cord to a brain.

The human nervous system is composed of a central nervous system (brain and spinal cord) and peripheral nervous system (nerves responsible for the inflow and leakage of a stimulus of a central nervous system).

An axon of nerve cells is wrapped in a membrane of myelin, and when the myelin is damaged or peeled off, nerves do not function properly, causing problems throughout the brain as well as the whole body.

Since the axon is preserved even when the myelin is shed, remyelinization proceeds and the process of demyelination is repeated, eventually resulting in the damage to the axon.

The damage to the myelin around nerves is called demyelination, which is the cause of many chronic diseases and is known to be caused by autoimmunity, genetic factors, viral infections, environmental factors, and the like. Since the exact cause of myelinization may not be specified, there is no fundamental therapy for the damage to the myelin.

Accordingly, an embodiment of the present disclosure provides an electroceutical screening device and a screening method using the same capable of evaluating remyelinization by arbitrarily constructing cell models under various conditions and screening the remyelinization under various electrical stimulation conditions in order to remyelinate nerves by activating a cell state through electrical stimulation, in therapy of peripheral nerves.

Conventionally, Korean Patent Publication No. 10-0150390 ("Cell Potential Measuring Device") discloses a cell potential measuring device capable of accurately or efficiently using measurement and at the same time providing convenience in arranging measurement results by using an integrated composite electrode that enables multi-point simultaneous measurement of potential change due to cell activity.

RELATED ART DOCUMENT

Patent Document

Korean Patent Publication No. 10-0150390 (Registration Date 1998.06.12.)

DISCLOSURE

Technical Problem

An object of the present disclosure provides an electroceutical screening device and a screening method using the same capable of selecting optimal electrical stimulation conditions for treating diseases by giving electrical stimulation to nerve cells or nerve clusters generated in multiple channels and measuring conduction velocity of each nerve.

Technical Solution

In one general aspect, an electroceutical screening device includes: a microfluidic chip including a cell culture part which is a space for receiving cell bodies, and a microchannel assembly which is connected to the cell culture part so that cell clusters, which are at least a portion of the cell bodies, grow as time passes, and which includes multiple channels, for receiving the cell clusters, formed around the cell culture part; and a substrate which is coupled to the microfluidic chip and includes an electrode assembly including electrodes provided in positions each corresponding to the cell culture part and the multiple channels, respectively, in which one end of each of second electrodes $E21$ to $E2n$, which are n of the electrodes or one end of each of third electrodes $E31$ to $E3m$, which are m of the electrodes, may be formed at a position corresponding to the channel.

One end of the first electrode $E1$, which is at least one of the electrodes, may be formed at a position corresponding to the cell culture part so that electrical stimulation is applied to the cell body received in the cell culture part through the first electrode $E1$.

One end of the first electrode $E1$ may be formed inside the substrate, one end of the second electrodes $E21$ to $E2n$ and one end of the third electrodes $E31$ to $E3m$ may be positioned along the channel so as to be connected to one side and the other side of the cell cluster, respectively, and one end of the third electrodes $E31$ to $E3m$ may be provided closer to the inner side of the cell culture part than one end of the second electrodes $E21$ to $E2n$.

A distance between one end of the second electrodes $E21$ to $E2n$ and one end of the third electrodes $E31$ to $E3m$ formed at a position corresponding to each channel may be constant.

Lengths of bent parts of ends of the second electrodes $E21$ to $E2n$ in a circumferential direction may be greater than a width of the channel, and may be longer than lengths of bent parts of ends of the third electrodes $E31$ to $E3m$ in a circumferential direction.

The electroceutical screening device may further include: a guide block in which each of the microfluidic chips is positioned in at least one predetermined area; and a buffer unit attached to a lower portion of the guide block and positioned excluding an area where the microfluidic chip is positioned.

The electroceutical screening device may further include: at least one PCB board that is positioned outside the guide block and receives an electrical signal from an external control unit, in which electrical stimulation may be supplied to the substrate by an electrical signal input through the PCB board.

The electroceutical screening device may further include: an upper case fixing the guide block and having a hole formed in a certain area; and a lower case fastened to the upper case with a predetermined pressure to couple the guide block, the PCB board, the substrate, and the microfluidic chip.

The electroceutical screening device may further include: a cap fastened to the hole of the upper case.

In another general aspect, a screening method using the electroceutical screening device includes: by measuring a signal received from the second electrode by electrical stimulation applied through the first electrode, measuring electrical conduction velocity of at least one of a cell body and a cell cluster using a time difference from an electrical stimulation time by the first electrode to an electrical stimulation measurement time in the second electrode.

By measuring a signal received by the second electrode via a third electrode by electrical stimulation applied through a first electrode, electrical conduction velocity of at least one of a cell body and a cell cluster may be measured using a time difference between an electrical stimulation pass time in the third electrode and an electrical stimulation measurement time in the second electrode.

Different electrical stimulations may be applied to each channel using the third electrode and the second electrode.

Advantageous Effects

The electroceutical screening device and the screening method using the same according to an exemplary embodiment of the present disclosure has the advantage of being able to find electrical stimulation therapy conditions optimized for therapy of peripheral nerve diseases by giving different electrical stimuli to each channel in which nerve cells grow and conducting various electrical stimulation tests under various conditions to evaluate electrical stimulation therapy conditions.

As a result, there is an advantage of being able to construct a platform for evaluating remyelination of peripheral nerves according to electrical stimulation conditions.

BEST MODE

Figure 1:
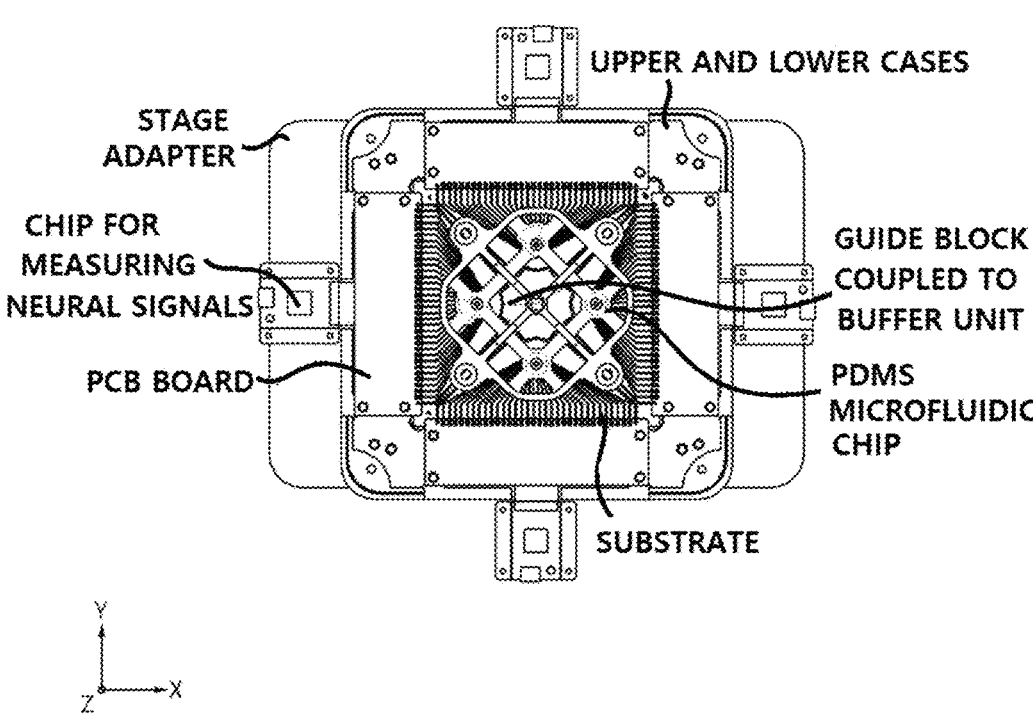
FIG. 1 is a perspective view illustrating an electroceutical screening device according to an embodiment of the present disclosure.

Hereinafter, an electroceutical screening device of the present disclosure and a screening method using the same will be described in detail with reference to the accompanying drawings. The drawings to be provided below are provided by way of example so that the spirit of the present disclosure can be sufficiently transferred to those skilled in the art. Therefore, the present disclosure is not limited to the drawings to be provided below, but may be implemented in other forms. In addition, like reference numerals denote like elements throughout the specification.

Technical terms and scientific terms used in the present specification have the general meaning understood by those skilled in the art to which the present disclosure pertains unless otherwise defined, and a description for the known function and configuration unnecessarily obscuring the gist of the present disclosure will be omitted in the following description and the accompanying drawings.

An electroceutical screening device and a screening method using the same according to an embodiment of the present disclosure are a device for screening conditions for the most optimal electrical stimulation therapy and a screening method using the same during developing electroceuticals for peripheral nerve disease therapy.

That is, through this, there is an advantage in that a cell model may be constructed, various electrical stimulation conditions may be provided, and remyelinization may be evaluated based thereon to find the conditions for the most optimal electrical stimulation therapy.

Figure 2:
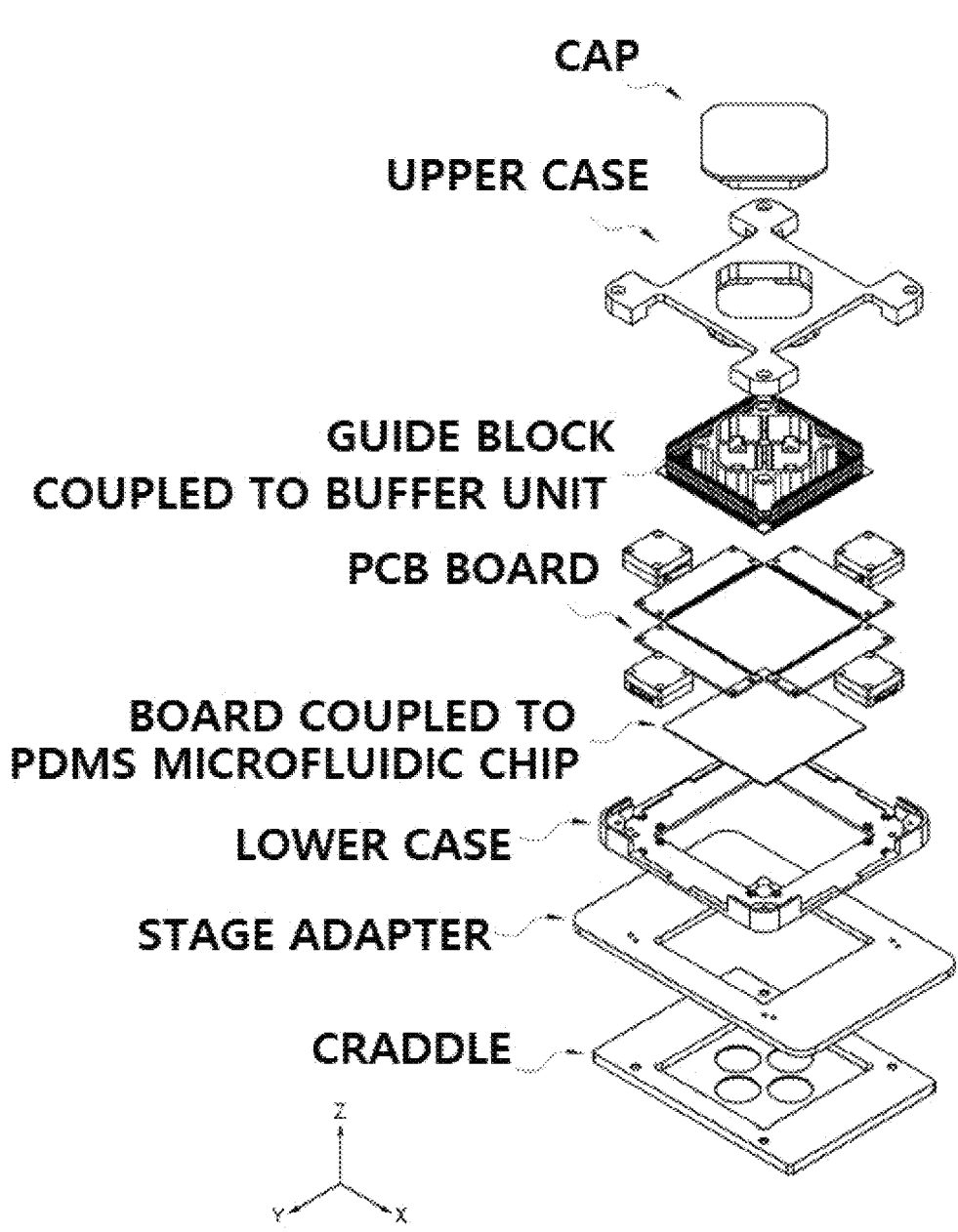
FIG. 2 is an exploded perspective view illustrating the electroceutical screening device according to the embodiment of the present disclosure.

As illustrated in FIGS. 1 and 2, the electroceutical screening device according to the embodiment of the present disclosure is preferably formed by assembling various components on upper and lower portions centered on a microfluidic chip and a substrate.

In this case, it is most preferable that the electroceutical screening device is manufactured to fit a stage of a microscope for imaging. To this end, it is preferable to include a separate stage adapter and mounting means at a lower end portion.

It is preferable that the mounting means is formed with a hole in consideration of an operating range of a lens of the microscope, and the microfluidic chip and the substrate may be aligned at a desired position by combining the stage adapter and the mounting means by giving counter boring.

In addition, the microfluidic chip is preferably a polydimethylsiloxane (PDMS) microfluidic chip, but is not limited thereto. However, for easy description, the microfluidic chip will be described by being limited to the PDMS microfluidic chip.

The respective components will be described in detail.

Figure 3:
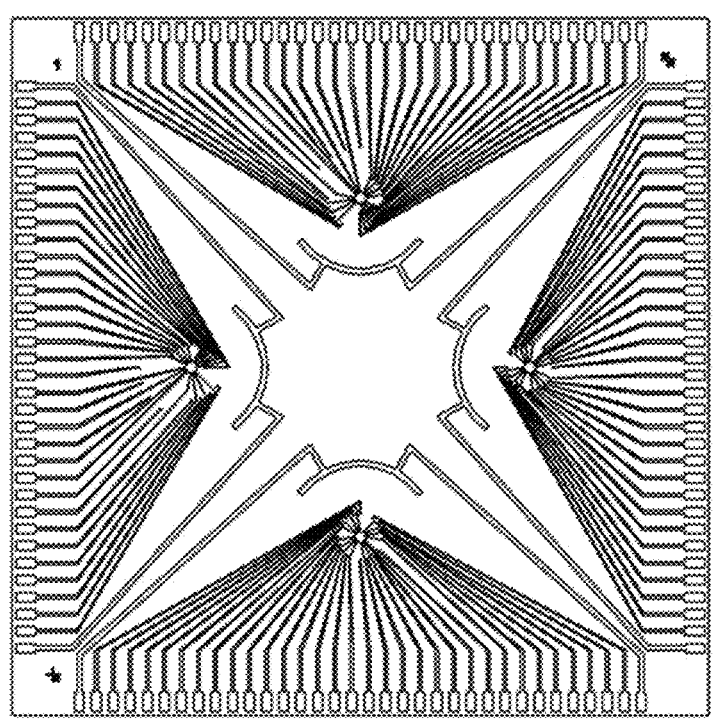
FIG. 3 is an exemplary diagram illustrating a substrate of the electroceutical screening device according to the embodiment of the present disclosure.
Figure 3:
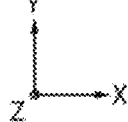

The substrate includes an electrode assembly including electrodes provided at corresponding positions of a cell culture part and each of the multiple channels, and is preferably combined with the PDMS microfluidic chip. As illustrated in FIG. 3, the substrate is most preferably in the form of a glass substrate, and the substrate preferably has a circuit formed thereon to provide electrical stimulation to a nerve cell body or to measure a received signal by the provided electrical stimulation.

The PDMS microfluidic chip preferably includes a cell culture part which is a space for receiving cell bodies, and a microchannel assembly which is connected to the cell culture part so that cell clusters, which are at least a portion of the cell bodies, grow as time passes, and which has multiple channels, for receiving the cell clusters, formed around the cell culture part.

In this case, it is most preferable that the cell cluster grows radially, and it is most preferable that the multiple channels are also formed radially, but this is only one embodiment of the present disclosure, and the cell cluster grows or forms in a different form due to external factors.

Figure 4:
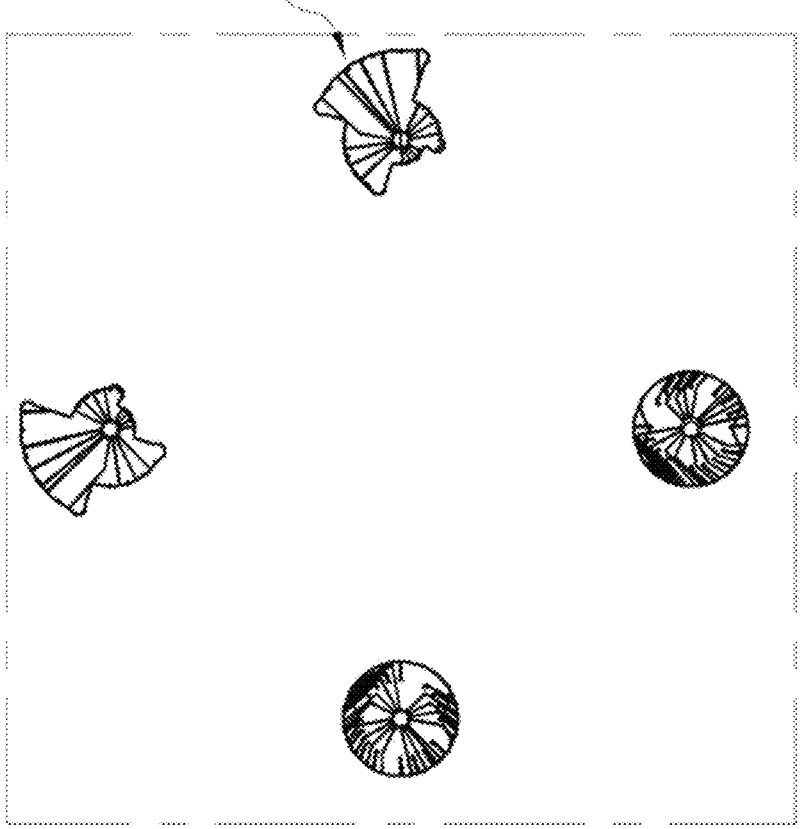
FIG. 4 is an exemplary view illustrating a PDMS microfluidic chip of the electroceutical screening device according to the embodiment of the present disclosure.
Figure 4:
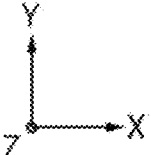

In detail, the PDMS microfluidic chip may have various thicknesses and shapes, as illustrated in FIG. 4, and it is preferable to provide guidelines for growing a nerve cell body in a desired direction.

Figure 5:
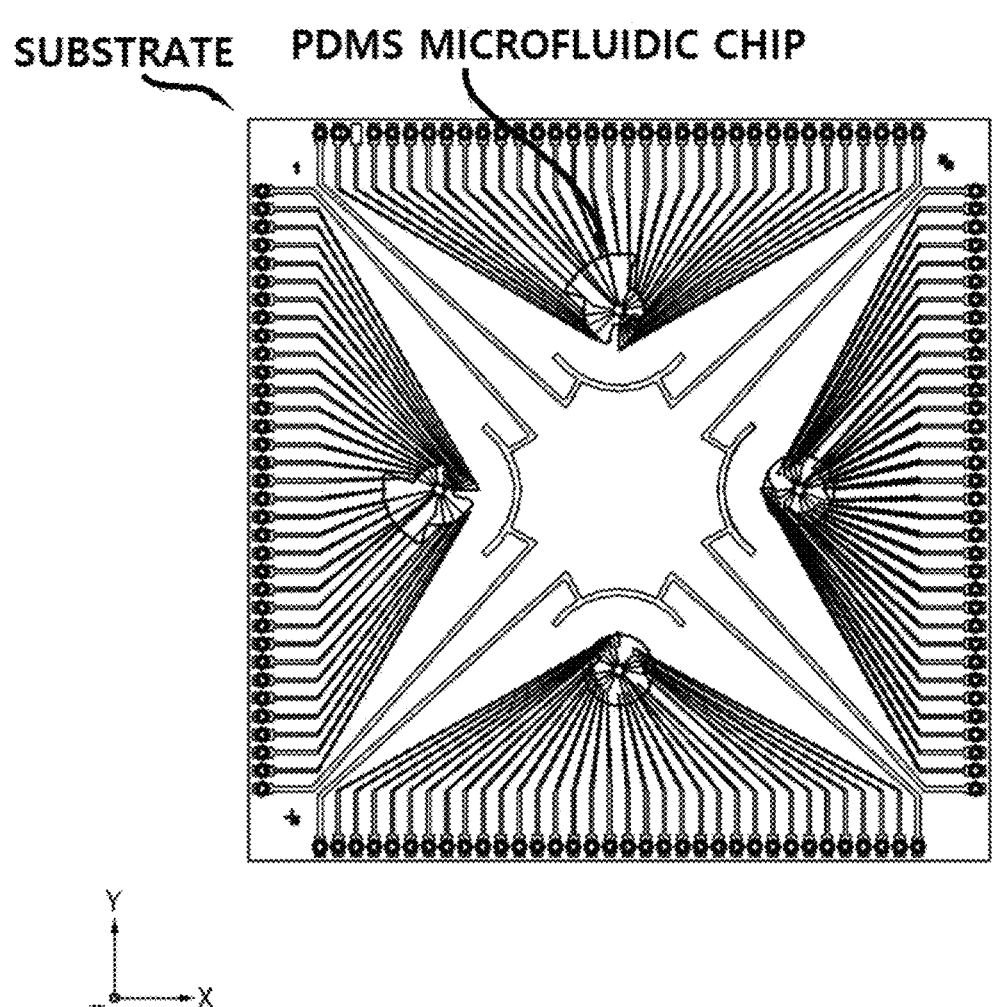
FIG. 5 is an exemplary assembly diagram illustrating a combination of a PDMS microfluidic chip and a substrate of the electroceutical screening device according to the embodiment of the present disclosure.

In addition, the PDMS microfluidic chip and the substrate are preferably formed as illustrated in FIG. 5.

As illustrated in FIGS. 3 and 5 to 7, the electrode assembly included in the substrate includes at least one first electrode E1, n second electrodes E21 to E2$n$, and m third electrodes E31 to E3$m$.

Figure 6:
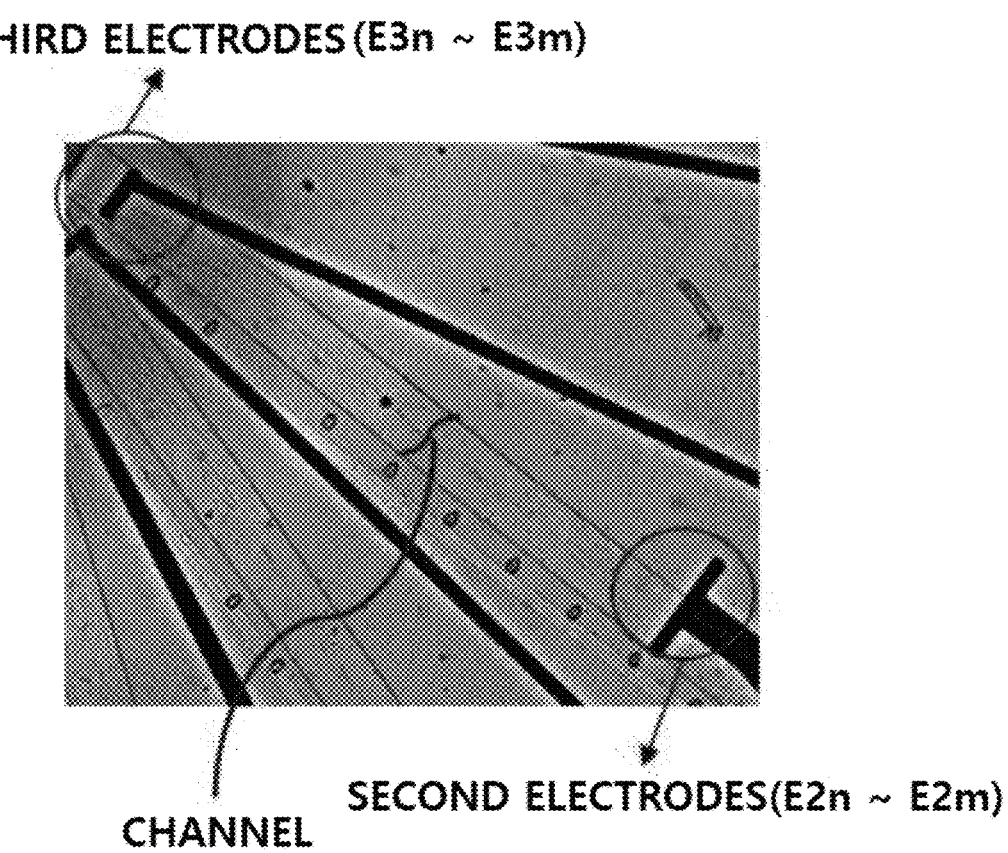
FIGS. 6 and 7 are exemplary diagrams illustrating an electrode assembly formed on the substrate of the electroceutical screening device according to the embodiment of the present disclosure.
Figure 7:
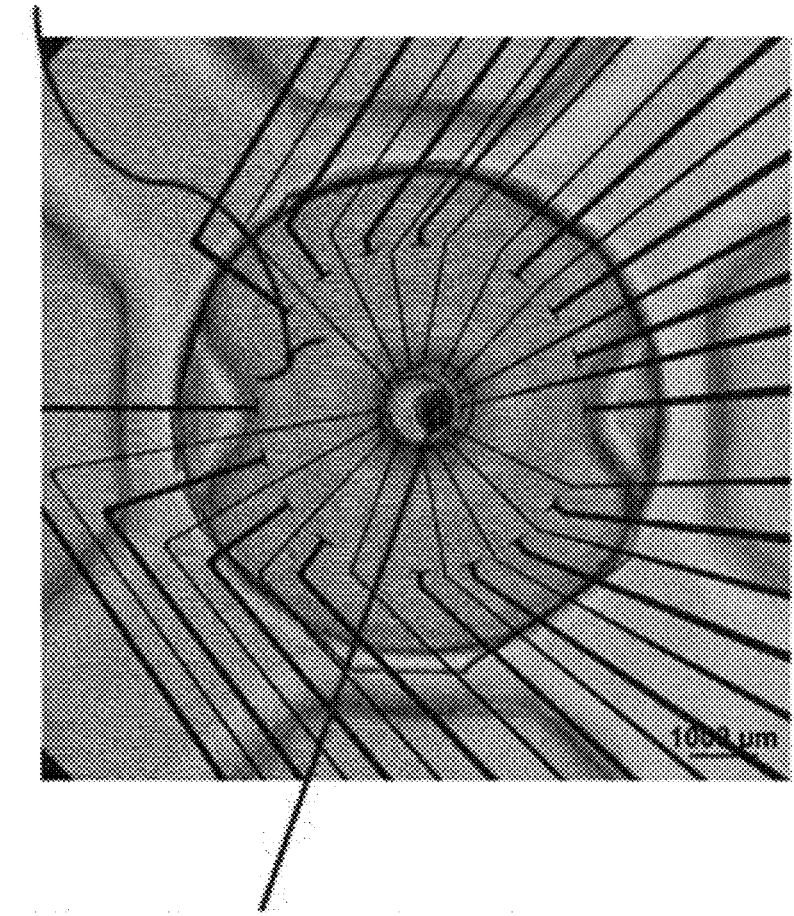

Here, since the first electrode E1 is provided at a central portion which is an inside of the PDMS microfluidic chip and a lower end of a cell, it is impossible to clearly illustrate the first electrode E1 through the drawing, so the first electrode E1 is not illustrated in FIG. 6 and is roughly indicated in FIG. 7.

It is preferable that one end of the first electrode E1 is formed at a position corresponding to the cell culture part so that electrical stimulation may be applied to the cell body received in the cell culture part through the first electrode E1. It is preferable that one end of each of the second electrodes E21 to E2$n$ is formed at a position corresponding to the channel to be able to measure the potential of the cell cluster in which the channel is received.

In addition, it is preferable that one end of each of the third electrodes E31 to E3$m$ may apply the electrical stimulation to the cell cluster received in the channel through the third electrodes E31 to E3$m$, or may be formed at a position corresponding to the channel to be able to measure the potential of the cell cluster.

Of course, the electrical stimulation may also be applied to the cell cluster received in the channel even through the second electrodes E21 to E2$n$.

In this case, it is preferable that a distance between one end of the second electrodes E2$n$ to E2$n$ and one end of the third electrodes E3$n$ to E3$m$ formed at positions corresponding to each channel is constant, but, for example, the distance is most preferably 500 μm to 20 mm.

As a result, as described above, it is preferable that one end of the first electrode E1 is formed at the center of the substrate, and it is preferable that one end of the second electrodes E2$n$ to E2$n$ and one end of the third electrode may be positioned along the channel to be connected to one side and the other side of the nerve cluster, respectively, and one end of the third electrodes E3$n$ to E3$m$ is provided at an inner side closer to the cell culture part than one end of the second electrodes E2$n$ to E2$n$.

More specifically, as illustrated in FIG. 6, one end of the second electrodes E2$n$ to E2$n$ and one end of the third electrodes E3$n$ to E3$m$ are positioned along the channel, respectively, and as illustrated in FIG. 7, it is preferable that lengths of bent parts of ends of electrodes (second electrode E2$n$ to E2$n$) in a circumferential direction formed on the outside centered on the grown nerve cell body are greater than a width of the channel, and the lengths of the bent parts of the ends of the electrode (second electrodes E2$n$ to E2$n$) formed on the outside are longer than lengths of bent parts of ends of electrodes (third electrodes E3$n$ to E3$m$) formed close to an inner center. It is preferable to give such a difference in degree of bending in order not to affect the channel.

Figure 8:
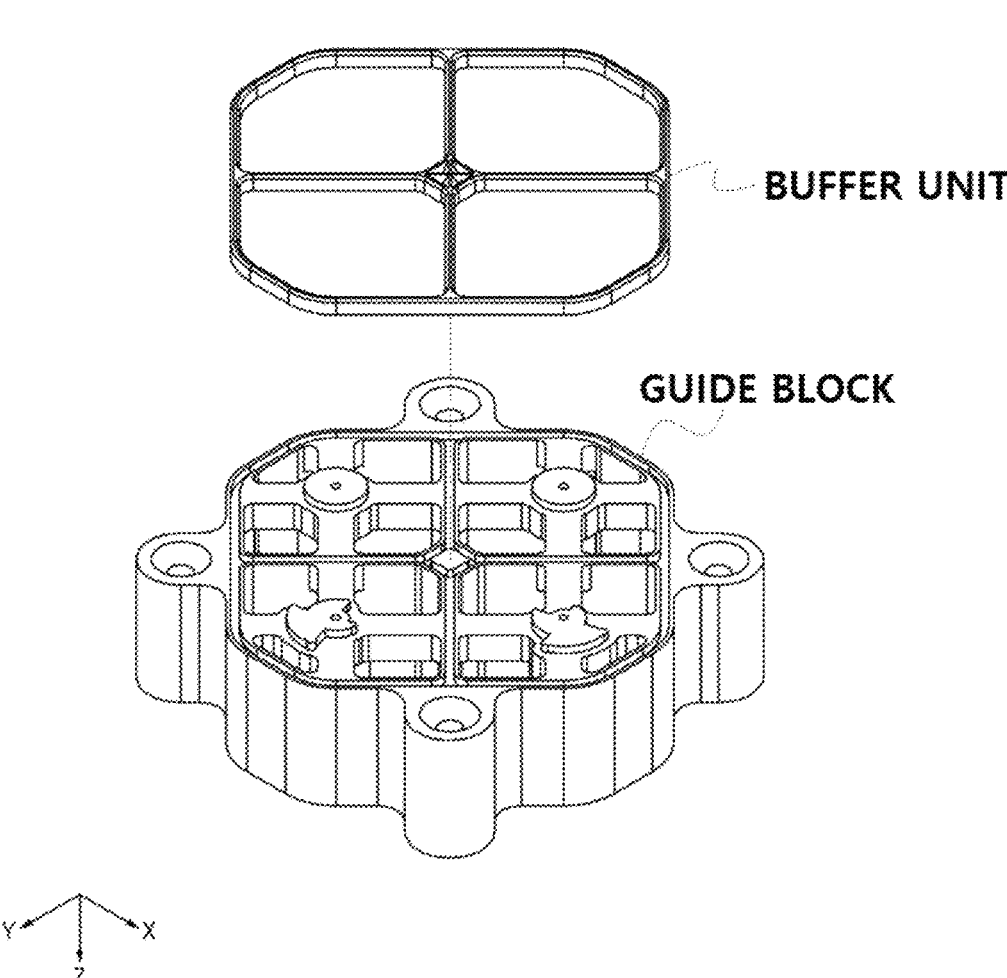
FIGS. 8 and 9 are exemplary diagrams of a rear surface of a guide block in which a PDMS microfluidic chip and a buffer unit of the electroceutical screening device according to the embodiment of the present disclosure are combined.
Figure 9:
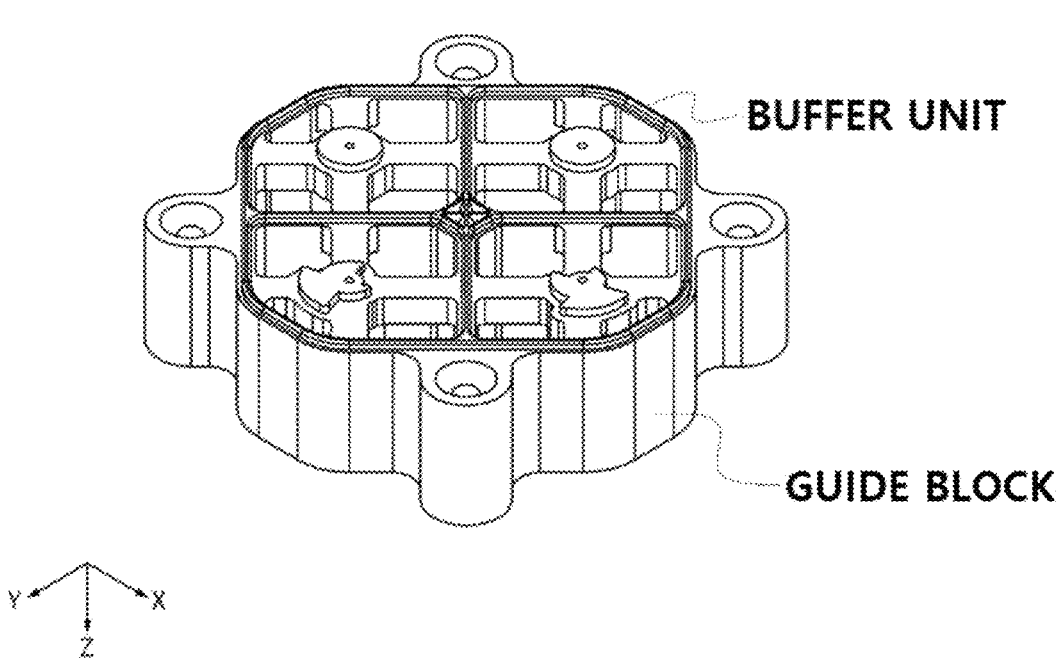

As illustrated in FIGS. 8 and 9, the PDMS microfluidic chip is preferably positioned on a guide block.

In other words, the guide block (FIG. 8) is preferably coupled so that at least one or more PDMS microfluidic chips are each positioned in a predetermined area. The guide block allows the PDMS microfluidic chip and the substrate to be coupled to an accurate position, and thus, the signal measurement and electrical stimulation of the cell body are performed at a desired position.

The PDMS microfluidic chip is a chip made of silicon, and since the risk of breakage increases when the fastening pressure is too high, fastening with a constant pressure is required.

To this end, the guide block is preferably configured to further include a buffer unit at the lower portion.

The buffer unit (FIG. 9) is preferably configured in the form of an O-ring, but as illustrated in FIG. 9, may be configured differently according to the shape of the guide block.

It is preferable that the buffer unit is configured not to be damaged even when pressure is applied to the substrate after the electroceutical screening device according to an embodiment of the present disclosure is coupled. As a result, it is preferable that the cell culture medium contained therein is not to leak to the outside.

It is preferable that the cell culture medium is preferably included in the channel. In detail, since the signal (measurement signal) from the electrode does not contact the first electrode at the lower portion, in order to smoothly detect this, it is preferable to transmit a signal through the cell culture medium. As a result, it is possible to measure the movement of ions generated by the conduction of nerve signals through the cell culture medium and the cell membrane through the substrate.

To this end, the cell culture medium is preferably composed of a liquid having high electrical conductivity, and it is preferable to put the cell culture medium into the channel so that the electrode may better receive signals.

In addition, it is preferable to further include at least one PCB substrate that is positioned outside the guide block and receives an electrical signal from an external control unit.

As illustrated in FIG. 2, it is preferable that the PCB substrate is positioned outside the substrate so that the electrode of the PCB substrate and the electrode of the substrate are accurately aligned. As a result, the electrical stimulation is supplied to the substrate by the electrical signal input through the PCB substrate.

In addition, as illustrated in FIG. 1, the electroceutical screening device according to the embodiment of the present disclosure is coupled using the upper case and the lower case. It is preferable that the upper case fixes the guide block, and the hole is formed in a certain area. It is preferable that the lower case is fastened to the upper case with a predetermined pressure to couple the guide block, the PCB substrate, the substrate, and the PDMS microfluidic chip.

The desired pressure between the PDMS microfluidic chip and the substrate may be provided through the coupling of the upper case and the lower case.

As illustrated in FIG. 2, the upper case preferably further includes a cap fastened to the hole area in order to prevent contamination by preventing the intrusion of bacteria although air passes through a hole formed in a certain area.

The cap is most preferably manufactured to be fastened to the hole of the upper case so that air is introduced while blocking the entry and exit of external microorganisms.

As described above, according to the screening method using the electroceutical screening device according to the embodiment of the present disclosure, different electrical stimulation is applied to each nerve cell body grown in each channel through electrodes provided at corresponding positions of each channel, so it is preferable to evaluate the conditions for the electrical stimulation therapy through the conduction velocity measurement.

Figure 10:
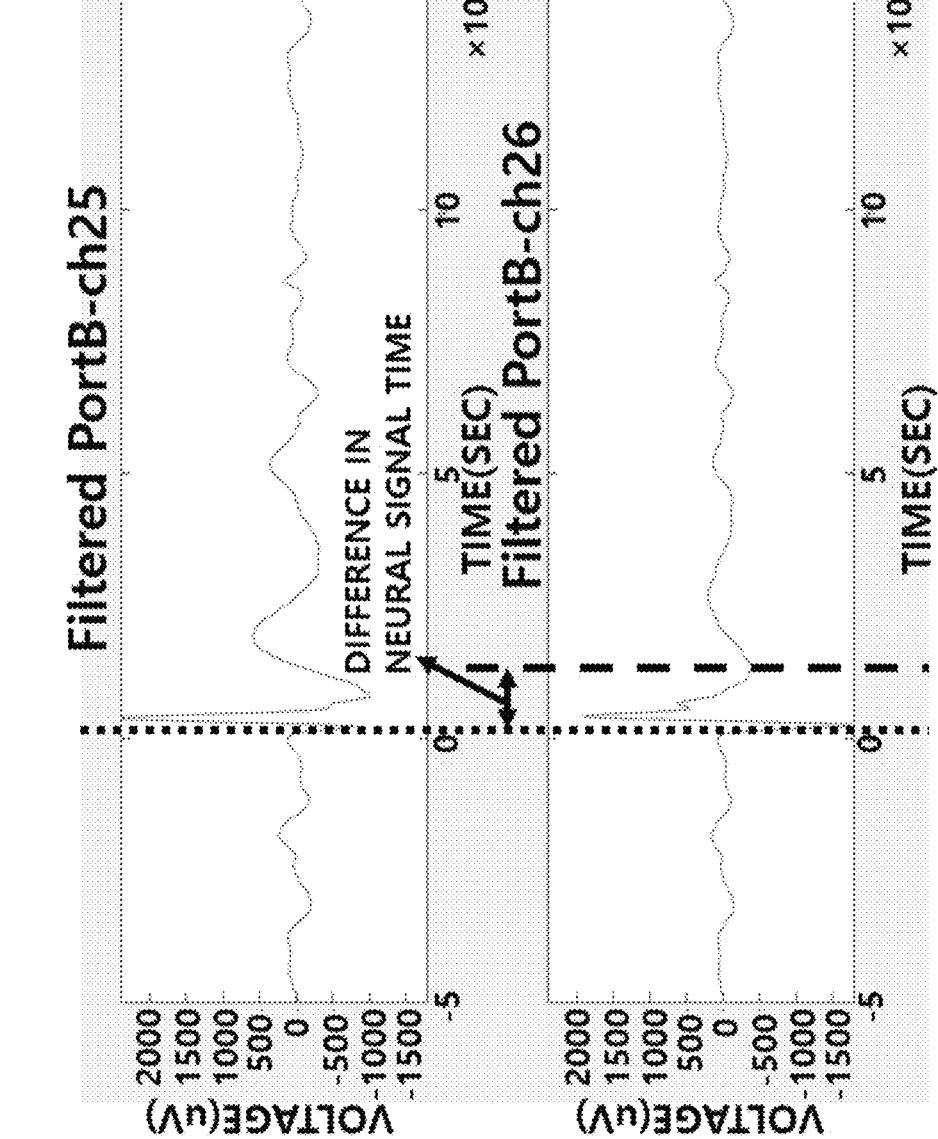
FIG. 10 is an exemplary graph in which electrical stimulation is measured by electrical stimulation in a screening method using an electroceutical screening device according to the embodiment of the present disclosure.

That is, various electrical stimulations are applied to each electrode, and as illustrated in FIG. 10, the electrical conduction velocity may be measured using the measured signal difference to evaluate the conditions for the electrical stimulation therapy.

In detail, the signals received by the second electrodes E2*n* to E2*n* are measured by the electrical stimulation applied through the first electrode E1, and the electrical conduction velocity may be measured using a time difference from the electrical stimulation time by the first electrode E1 to the electrical stimulation measurement time in the second electrodes E2*n* to E2*n*. In this case, it is possible to perform various electrical stimulation tests by applying different electrical stimulations to each channel, and to evaluate each condition for the electrical stimulation therapy by measuring the conduction velocity according to various electrical stimulation tests. As described above, since the distance between one end of the second electrodes E2*n* to E2*n* and one end of the third electrodes E3*n* to E3*m* formed at a position corresponding to each channel is constant, the conduction velocity may be measured using the time difference.

In addition, the signals received by the second electrodes E2*n* to E2*n* via the third electrodes E3*n* to E3*m* are measured by the electrical stimulation applied through the first electrode E1, and the electrical conduction velocity may be measured using a time difference from the electrical stimulation time by the first electrode E1 to the electrical stimulation pass time in the third electrodes E3*n* to E3*m* to the electrical stimulation measurement time in the second electrodes E2*n* to E2*n*. In this case, it is possible to perform various electrical stimulation tests by applying different electrical stimulations to each channel, and to evaluate the conditions for the electrical stimulation therapy by measuring the conduction velocity according to various electrical stimulation tests. As described above, since the distance between one end of the second electrodes E2*n* to E2*n* and one end of the third electrodes E3*n* to E3*m* formed at a position corresponding to each channel is constant, the electrical conduction velocity may be measured using the time difference.

In addition, different electrical stimulations may be applied to each channel using the third electrodes E3*n* to E3*m* and the second electrodes E2*n* to E2*n*, thereby evaluating the conditions for the electrical stimulation therapy for various electrical stimulations.

That is, in other words, the electroceutical screening device and the screening method using the same according to an embodiment of the present disclosure give different electrical stimulation for each channel to nerve cells or nerve clusters generated in multiple channels to variously perform the electrical stimulation test under various conditions and evaluate the conditions for the electrical stimulation therapy, thereby finding the conditions for the electrical stimulation therapy optimized for peripheral nerve disease therapy.

Hereinabove, although the present disclosure has been described by specific matters such as detailed components, exemplary embodiments, and the accompanying drawings, they have been provided only for assisting in the entire understanding of the present disclosure. Therefore, the present disclosure is not limited to the exemplary embodiments. Various modifications and changes may be made by those skilled in the art to which the present disclosure pertains from this description.

Therefore, the spirit of the present disclosure should not be limited to these exemplary embodiments, but the claims and all of modifications equal or equivalent to the claims are intended to fall within the scope and spirit of the present disclosure.

The invention claimed is:

1. An electroceutical screening device, comprising:
   a microfluidic chip including a cell culture part which is a space for receiving cell bodies, and a microchannel assembly which is connected to the cell culture part so that cell clusters, which are at least a portion of the cell bodies, grow as time passes, and which includes multiple channels, for receiving the cell clusters, formed around the cell culture part; and
   a substrate which is coupled to the microfluidic chip and includes an electrode assembly including electrodes provided in positions each corresponding to the cell culture part and the multiple channels, respectively,
   wherein one end of a first electrode, which is at least one of the electrodes, is formed at a lower position corresponding to the cell culture part, and electrical stimulation is applied to the cell body received in the cell culture part through the first electrode,
   wherein one end of each of n second electrodes, where n is a natural number, is formed at a position corresponding to the channel and connected to one side of the cell clusters,
   wherein one end of each of m third electrodes, where m is a natural number, is formed at a position corresponding to the channel, connected to the other side of the cell clusters, and located on the inner side closer to the cell culture part than the second electrodes, and
   wherein electrical stimulation tests are performed by receiving the electrical stimulus applied through the first electrode by the second electrodes via the third electrodes.

2. The electroceutical screening device of claim 1, wherein one end of the first electrode is formed inside the substrate,
   one end of the second electrodes and one end of the third electrodes are positioned along the channel so as to be connected to one side and the other side of the cell cluster, respectively, and
   one end of the third electrodes is provided closer to the inner side of the cell culture part than one end of the second electrodes.

3. The electroceutical screening device of claim 1, wherein a distance between one end of the second electrodes and one end of the third electrodes formed at a position corresponding to each channel is constant.

4. The electroceutical screening device of claim 2, wherein lengths of bent parts of ends of the second electrodes in a circumferential direction are greater than a width of the channel, and are longer than lengths of bent parts of ends of the third electrodes in a circumferential direction.

5. The electroceutical screening device of claim 1, further comprising:

a guide block in which the microfluidic chip is positioned in at least one predetermined area; and a buffer unit attached to a lower portion of the guide block and positioned excluding an area where the microfluidic chip is positioned.

6. The electroceutical screening device of claim 5, further comprising:

at least one PCB board that is positioned outside the guide block and configured to receive an electrical signal from an external control unit, wherein electrical stimulation is supplied to the substrate by an electrical signal input through the PCB board.

7. The electroceutical screening device of claim 6, further comprising:

an upper case fixing the guide block and having a hole formed in a certain area; and a lower case fastened to the upper case with a predetermined pressure to couple the guide block, the PCB board, the substrate, and the microfluidic chip.

8. The electroceutical screening device of claim 7, further comprising:

a cap fastened to the hole of the upper case.

9. A screening method using the electroceutical screening device of claim 1, the screening method comprising:

measuring a signal received from the second electrode by electrical stimulation applied through the first electrode, measuring electrical conduction velocity of at least one of a cell body and a cell cluster using a time difference from an electrical stimulation time by the first electrode to an electrical stimulation measurement time in the second electrode.

10. A screening method using the electroceutical screening device of claim 1, the screening method comprising:

measuring a signal received by the second electrode via the third electrode by electrical stimulation applied through the first electrode, measuring electrical conduction velocity of at least one of a cell body and a cell cluster using a time difference between an electrical stimulation pass time in the third electrode and an electrical stimulation measurement time in the second electrode.

11. A screening method using the electroceutical screening device of claim 1, the screening method comprising:

applying different electrical stimulations to each channel using the third electrode and the second electrode.

* * * * *